US010022569B2

United States Patent
Matsui et al.

(10) Patent No.: US 10,022,569 B2
(45) Date of Patent: Jul. 17, 2018

(54) DRIVING DEVICE AND METHOD FOR CONTROLLING THE SAME

(71) Applicant: OLYMPUS CORPORATION, Hachioji-shi, Tokyo (JP)

(72) Inventors: Shunsuke Matsui, Hino (JP); Ko Kawashima, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/361,240

(22) Filed: Nov. 25, 2016

(65) Prior Publication Data

US 2017/0072226 A1   Mar. 16, 2017

Related U.S. Application Data

(63) Continuation of application No. PCT/JP2016/050701, filed on Jan. 12, 2016.

(30) Foreign Application Priority Data

Mar. 10, 2015 (JP) .................................. 2015-047637

(51) Int. Cl.
*A61H 1/00* (2006.01)
*A61N 7/00* (2006.01)
(Continued)

(52) U.S. Cl.
CPC ........ *A61N 7/00* (2013.01); *A61B 17/320068* (2013.01); *A61B 17/320092* (2013.01);
(Continued)

(58) Field of Classification Search
None
See application file for complete search history.

(56) References Cited

U.S. PATENT DOCUMENTS

2013/0331875 A1*  12/2013  Ross .............. A61B 17/320068
                                                                        606/169
2016/0324537 A1*  11/2016  Green ............ A61B 17/320068

FOREIGN PATENT DOCUMENTS

| JP | 4-247268 A  | 9/1992  |
| JP | 63-316674 A | 12/1998 |
| JP | 11-70118 A  | 3/1999  |

OTHER PUBLICATIONS

Apr. 12, 2016 International Search Report issued in International Patent Application No. PCT/JP2016/050701.

(Continued)

*Primary Examiner* — Michael Kahelin
*Assistant Examiner* — Shahdeep Mohammed
(74) *Attorney, Agent, or Firm* — Oliff PLC

(57) ABSTRACT

A driving device includes an output voltage decomposing unit which decomposes an output voltage applied to an ultrasonic transducer into a basic and harmonic components; an output current decomposing unit which decomposes an output current flowing through the ultrasonic transducer into a basic and harmonic components; a capacitor current calculator which calculates a basic and harmonic components of a capacitor current, based on the basic and harmonic components of the output voltage; a driving current calculator which calculates a basic and harmonic components of a driving current based on the basic and harmonic components of the output current and the capacitor current, a driving current summing unit which sums up the basic and harmonic components of the driving current, and a constant current controller which generates constant current control data.

6 Claims, 10 Drawing Sheets

(51) Int. Cl.
*A61B 18/00* (2006.01)
*B06B 1/02* (2006.01)
*A61B 17/32* (2006.01)
*A61B 17/00* (2006.01)

(52) U.S. Cl.
CPC ................ *A61B 18/00* (2013.01); *B06B 1/02* (2013.01); *B06B 1/0207* (2013.01); *A61B 2017/00017* (2013.01)

(56) References Cited

OTHER PUBLICATIONS

Sep. 21, 2017 Notification of Transmittal of English translation of International Preliminary Report on Patentability issued in International Patent Application No. PCT/JP2016/050701.

\* cited by examiner

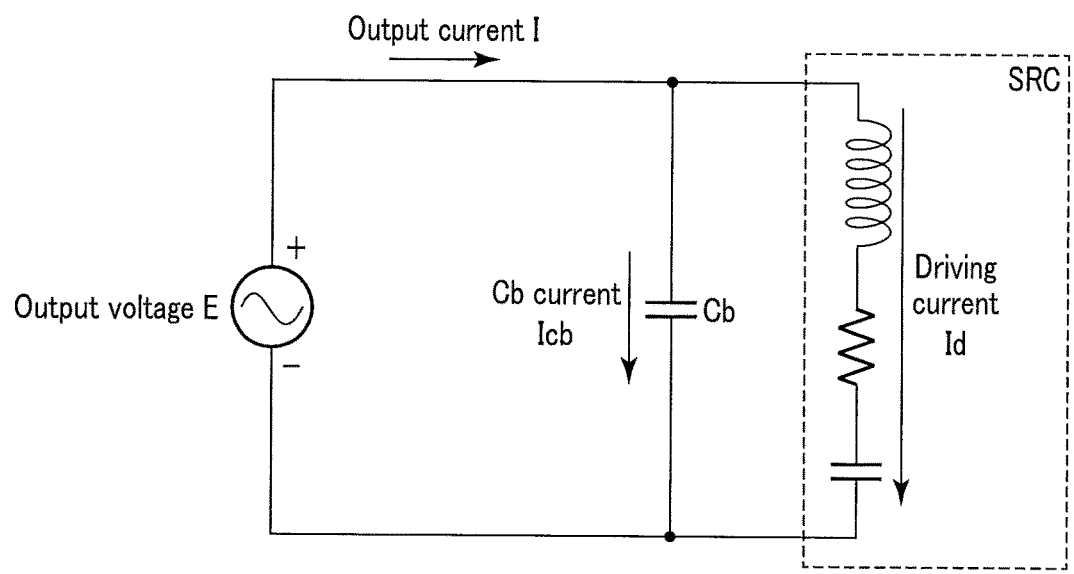
F I G. 3

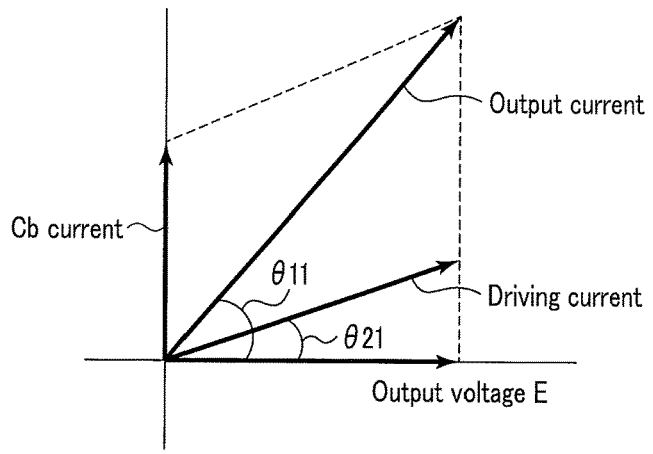
F I G. 4A
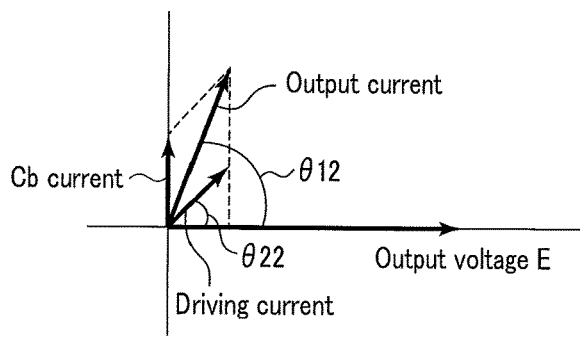
F I G. 4B
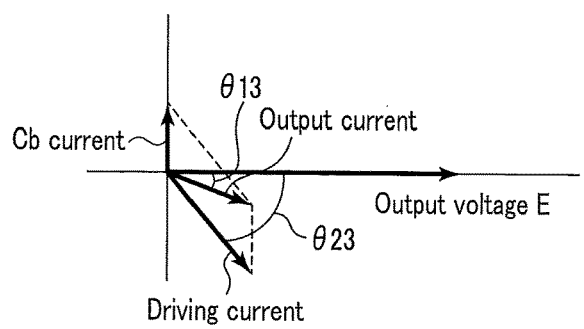
F I G. 4C

DRIVING DEVICE AND METHOD FOR CONTROLLING THE SAME

CROSS-REFERENCE TO RELATED APPLICATIONS

This application is a Continuation Application of PCT Application No. PCT/JP2016/050701, filed Jan. 12, 2016 and based upon and claiming the benefit of priority from the prior Japanese Patent Application No. 2015-047637, filed Mar. 10, 2015, the entire contents of both of which are incorporated herein by reference.

BACKGROUND OF THE INVENTION

1. Field of the Invention

The present invention relates to a driving device and a method for controlling the same.

2. Description of the Related Art

Ultrasonic operation apparatuses are known as one of apparatuses capable of performing treatment on a living tissue, such as incision, hemostasis, and coagulation. Ultrasonic operation apparatuses generally include an ultrasonic transducer, a driving device, and a probe. The ultrasonic transducer includes a piezoelectric element such as a piezoelectric device. The driving device supplies the ultrasonic transducer with driving power to cause the ultrasonic transducer to perform ultrasonic vibration. The probe transmits the ultrasonic vibration generated in the ultrasonic transducer to the distal end portion of the ultrasonic operation apparatus. In the ultrasonic operation apparatus as described above, constant current control is performed to maintain a constant current supplied from the driving device to the ultrasonic transducer such that vibration of stable amplitude is performed in the probe, even when load on the ultrasonic transducer fluctuates. For example, the ultrasonic operation apparatus presented in Japanese Patent Application KOKAI Publication No. 11-70118 performs control to fix a current supplied from the driving device to the ultrasonic transducer, by determining impedance in driving of the ultrasonic transducer, which corresponds to mechanical load on the probe, and feeding back the impedance to the driving device.

BRIEF SUMMARY OF THE INVENTION

According to a first aspect of the invention, a driving device including an ultrasonic transducer and electrically connected with an ultrasonic treatment tool treating a living tissue by ultrasonic vibration generated by the ultrasonic transducer, the ultrasonic transducer indicated with an electrical equivalent circuit in which a second capacitor is connected in parallel with a series circuit formed of an inductor, a first capacitor, and a resistor, comprises; an output voltage decomposing unit which decomposes an output voltage applied to the ultrasonic transducer by an alternating-current driving voltage to drive the ultrasonic transducer into a basic component and a harmonic component; an output current decomposing unit which decomposes an output current flowing through the ultrasonic transducer by the driving voltage into a basic component and a harmonic component; a capacitor current calculator which calculates a basic component and a harmonic component of a capacitor current flowing through the second capacitor, based on the basic component and the harmonic component of the output voltage obtained by the output voltage decomposing unit and an electrostatic capacitance value of the second capacitor; a driving current calculator which calculates a basic component and a harmonic component of a driving current flowing through the series circuit, based on the basic component and the harmonic component of the output current obtained by the output current decomposing unit and the basic component and the harmonic component of the capacitor current calculated by the capacitor current calculator; a driving current summing unit which sums up the basic component and the harmonic component of the driving current calculated by the driving current calculator; and a constant current controller which generates constant current control data to control the driving voltage such that the driving current summed up by the driving current summing unit has a target value.

According to a second aspect of the invention, a method for controlling a driving device including an ultrasonic transducer and electrically connected with an ultrasonic treatment tool treating a living tissue by ultrasonic vibration generated by the ultrasonic transducer, the ultrasonic transducer indicated with an electrical equivalent circuit in which a second capacitor is connected in parallel with a series circuit formed of an inductor, a first capacitor, and a resistor, comprises: decomposing an output voltage applied to the ultrasonic transducer by an alternating-current driving voltage to drive the ultrasonic transducer into a basic component and a harmonic component; decomposing an output current flowing through the ultrasonic transducer by the driving voltage into a basic component and a harmonic component; calculating a basic component and a harmonic component of a capacitor current flowing through the second capacitor, based on the basic component and the harmonic component of the output voltage and an electrostatic capacitance value of the second capacitor; calculating a basic component and a harmonic component of a driving current flowing through the series circuit, based on the basic component and the harmonic component of the output current and the basic component and the harmonic component of the capacitor current; summing up the basic component and the harmonic component of the driving current; and generating constant current control data to control the driving voltage such that the summed driving current has a target value.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is an electrical equivalent circuit diagram of an ultrasonic transducer driven around a resonant frequency;

FIG. 4A is a diagram illustrating relation between a basic component of an output current, a basic component of a Cb current, and a basic component of a driving current;

FIG. 4B is a diagram illustrating relation between a secondary harmonic component of the output current, a secondary harmonic component of the Cb current, and a secondary harmonic component of the driving current;

FIG. 4C is a diagram illustrating relation between a third harmonic component of the output current, a third harmonic component of the Cb current, and a third harmonic component of the driving current;

DETAILED DESCRIPTION OF THE INVENTION

An embodiment of the present invention will be explained hereinafter with reference to drawings.

Figure 1:
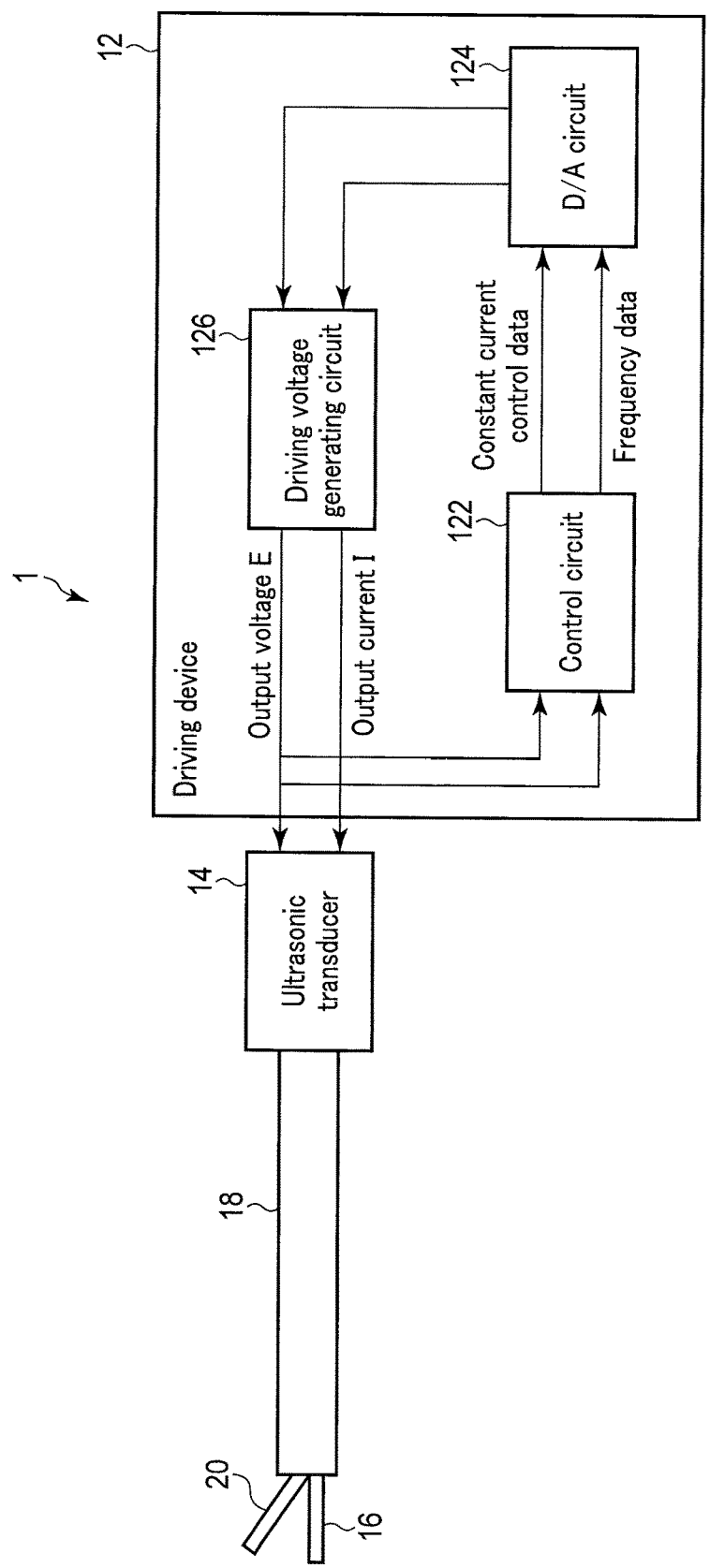
FIG. 1 is a block diagram illustrating a main configuration of an ultrasonic operation apparatus serving as an application example of a driving device according to an embodiment of the present invention.

FIG. 1 is a block diagram illustrating a main configuration of an ultrasonic operation apparatus serving as an application example of a driving device according to one embodiment of the present invention. An ultrasonic operation apparatus 1 includes a driving device 12. The driving device 12 is electrically connected with an ultrasonic treatment tool.

The driving device 12 generates an output signal to cause an ultrasonic transducer 14 of the ultrasonic treatment tool to perform ultrasonic vibration with fixed amplitude. The driving device 12 includes a control circuit 122, a D/A circuit 124, and a driving voltage generating circuit 126.

The control circuit 122 is formed of, for example, an FPGA (Field Programmable Gate Array). The control circuit 122 takes in an output voltage applied to the ultrasonic transducer 14 and an output current flowing through the ultrasonic transducer 14 in accordance with a driving voltage generated by the driving voltage generating circuit 126, as digital signals, and output constant current control data generated based on the taken output voltage and the output current to the D/A circuit 124. The constant current control data is data indicating a voltage value of the driving voltage to be generated in the driving voltage generating circuit 126 to drive the ultrasonic transducer 14 with the constant current, for example. The control circuit 122 outputs frequency data generated based on the taken output voltage and the output current to the D/A circuit 124. The frequency data is, for example, data indicating a frequency value of the driving voltage. The control circuit 122 will be explained in detail later.

The D/A circuit 124 converts the constant current control data and the frequency data that are output as digital signals from the control circuit 122 into analog signals, and outputs a constant current control signal and a frequency signal obtained by the conversion to the driving voltage generating circuit 126.

The driving voltage generating circuit 126 generates a driving voltage based on the constant current control signal and the frequency signal that are output from the D/A circuit 124, and applies the driving voltage to the ultrasonic transducer 14. The driving voltage is, for example, an alternating-current voltage generated by multiplying the constant current control signal by the frequency signal.

The ultrasonic treatment tool mainly includes the ultrasonic transducer 14 and a probe 16. The ultrasonic transducer 14 is, for example, a piezoelectric element, and performs ultrasonic vibration in accordance with the driving voltage applied from the driving voltage generating circuit 126.

The probe 16 is coupled with the ultrasonic transducer 14 through the inside of an elongated sheath 18, and vibrates together with vibration of the ultrasonic transducer 14. A holding unit 20 is rotatably attached to a distal end portion (an end portion on a side not facing the ultrasonic transducer 14) of the sheath 18, and is rotated in response to an operation of an operating unit (not illustrated). For example, a living tissue such as a blood vessel is held between the probe 16 and the holding unit 20, by rotation of the holding unit 20 by a user's operation of the operating unit (not illustrated).

Figure 2:
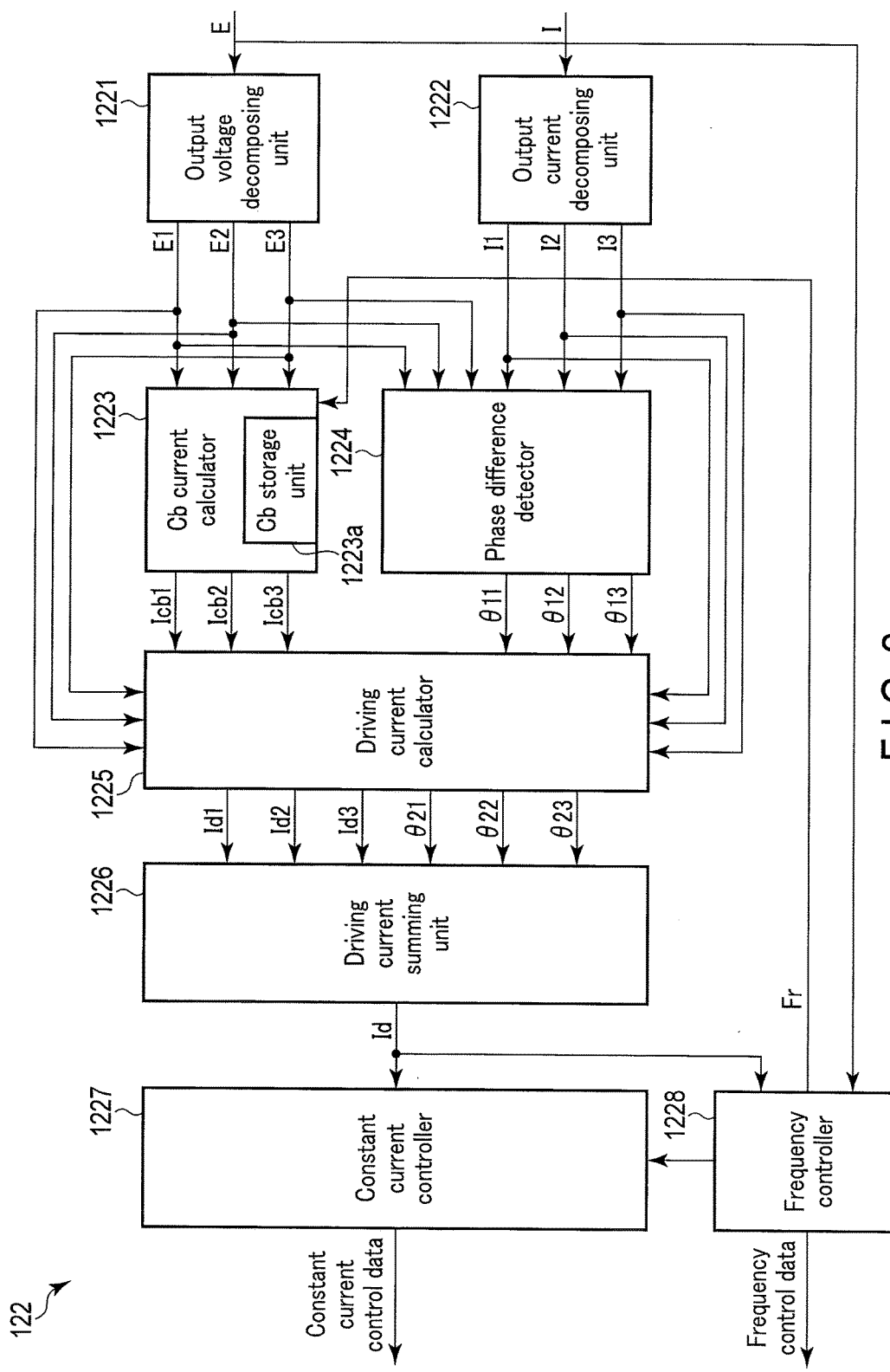
FIG. 2 is a block diagram illustrating a detailed configuration of a control circuit.

FIG. 2 is a block diagram illustrating a detailed configuration of the control circuit 122. The control circuit 122 includes an output voltage decomposing unit 1221, an output current decomposing unit 1222, a Cb current calculator 1223, a phase difference detector 1224, a driving current calculator 1225, a driving current summing unit 1226, a constant current controller 1227, and a frequency controller 1228.

The output voltage decomposing unit 1221 takes in an output voltage E applied to the ultrasonic transducer 14 as a digital signal, and decomposes the taken output voltage E into a basic component and harmonic components. For example, the output voltage decomposing unit 1221 decomposes the output voltage E into a basic component E1, a secondary harmonic component E2, and a third harmonic component E3. The output current decomposing unit 1222 takes in an output current I flowing through the ultrasonic transducer 14 as a digital signal, and decomposes the taken output current I into a basic component and harmonic components. For example, the output current decomposing unit 1222 decomposes the output current I into a basic component I1, a secondary harmonic component I2, and a third harmonic component I3. These decompositions are performed using, for example, fast Fourier transform (FFT).

FIG. 3 is an electrical equivalent circuit diagram of the ultrasonic transducer 14 that is driven around the resonant frequency. As illustrated in FIG. 3, the ultrasonic transducer 14 vibrating around the resonant frequency Fr can be regarded as a circuit in which a damper capacitor (second capacitor) Cb indicating a stray capacitance component caused by the piezoelectric element and the electrode plate of the ultrasonic transducer 14 is connected in parallel with a series resonant circuit SRC formed of an inductor and a capacitor (first capacitor) indicating mechanical vibration property of the ultrasonic transducer 14 and a resistor indicating a mechanical load thereof. In the equivalent circuit of FIG. 3, in the output current I flowing through the ultrasonic transducer 14 by application of the output voltage E, only driving current Id flowing through the series resonant circuit SRC contributes to vibration of the ultrasonic transducer 14. A capacitor current (hereinafter referred to as "Cb current") Icb flowing through the damper capacitor Cb does not contribute to driving at all. Specifically, a phase difference between the output voltage E and the current Icb is 90°. Accordingly, it is required to determine the accurate driving current Id, to accurately perform constant current control on the ultrasonic transducer 14. Because the driving current Id includes harmonic components caused by influence of the output voltage E and the output current I, the absolute value and the phase of the driving current Id differ for each of the basic component and the harmonic components. For this reason, in the present embodiment, the basic component and each of the harmonic components of the driving current Id are determined by once determining the basic component and each of the harmonic components of the Cb current Icb, and thereafter the basic component and the harmonic components of the driving current Id are summed up, to calculate the accurate driving current Id in consideration of the influence of the harmonic components. Decompositions in the output voltage decomposing unit 1221 and the output current decomposing unit 1222 are processing to determine the basic components and the harmonic components of the Cb current Icb and the driving current Id.

The Cb current calculator 1223 calculates the absolute values of the basic component and each of the harmonic components of the Cb current Icb serving as a current that does not contribute to vibration of the ultrasonic transducer 14, in the output current I flowing through the ultrasonic transducer 14. Supposing that the ultrasonic transducer 14 can be indicated with the equivalent circuit of FIG. 3, the absolute value Icb1 of the basic component, the absolute value Icb2 of the secondary harmonic component, and the absolute value Icb3 of the third harmonic component of the Cb current Icb are calculated as follows, for example, from the basic component E1, the secondary harmonic component E2, and the third harmonic component E3 of the output voltage, the resonant frequency Fr, and the electrostatic capacitance value Cb of the damper capacitor Cb.

$$Icb1 = 2\pi \times Fr \times Cb \times E1$$

$$Icb2 = 2\pi \times Fr \times Cb \times E2$$

$$Icb3 = 2\pi \times Fr \times Cb \times E3$$

The electrostatic capacitance value Cb of the damper capacitor Cb is, for example, a fixed value stored in a Cb storage unit 1223a. The electrostatic capacitance value Cb is measured by measuring the output current at the time when the ultrasonic operation apparatus 1 is driven with an antiresonant frequency.

The phase difference detector 1224 detects a phase difference θ11 between the basic component E1 of the output voltage E and the basic component I1 of the output current I, a phase difference θ12 between the secondary harmonic component E2 of the output voltage E and the secondary harmonic component I2 of the output current I, and a phase difference θ13 between the third harmonic component E3 of the output voltage E and the third harmonic component I3 of the output current I.

The driving current calculator 1225 calculates the absolute value Id1 of the basic component of the driving current Id using the absolute value I1 of the basic component of the output current I, the absolute value Icb1 of the basic component of the Cb current Icb, and the phase difference θ11. The driving current calculator 1225 also calculates the absolute value Id2 of the secondary harmonic component of the driving current Id using the absolute value I2 of the secondary harmonic component of the output current I, the absolute value Icb2 of the secondary harmonic component of the Cb current Icb, and the phase difference θ12. The driving current calculator 1225 also calculates the absolute value Id3 of the third harmonic component of the driving current Id using the absolute value I3 of the third harmonic component of the output current I, the absolute value Icb3 of the third harmonic component of the Cb current Icb, and the phase difference θ13. FIG. 4A illustrates relation between the basic component I1 of the output current I, the basic component Icb1 of the Cb current Icb, and the basic component Id1 of the driving current Id. FIG. 4B illustrates relation between the secondary harmonic component I2 of the output current I, the secondary harmonic component Icb2 of the Cb current Icb, and the secondary harmonic component Id2 of the driving current Id. FIG. 4C illustrates relation between the third harmonic component I3 of the output current I, the third harmonic component Icb3 of the Cb current Icb, and the third harmonic component Id3 of the driving current Id. As is clear from the relations in FIG. 4A, FIG. 4B, and FIG. 4C, the driving current Id is obtained by subtracting the Cb current Icb from the output current I in a vector manner. Accordingly, the absolute value Id1 of the basic component of the driving current Id, the absolute value Id2 of the secondary harmonic component of the driving current Id, and the absolute value Id3 of the third harmonic component of the driving current Id are calculated from the following relations.

$$Id1^2 = I1^2 + Icb1^2 - 2 \times I1 \times Icb1 \times \sin\theta 11$$

$$Id2^2 = I2^2 + Icb2^2 - 2 \times I2 \times Icb2 \times \sin\theta 12$$

$$Id3^2 = I3^2 + Icb3^2 - 2 \times I3 \times Icb3 \times \sin\theta 13$$

The driving current calculator 1225 also calculates a phase difference θ21 between the basic component E1 of the output voltage E and the basic component Id1 of the driving current Id, a phase difference θ22 between the secondary harmonic component E2 of the output voltage E and the secondary harmonic component Id2 of the driving current Id, and a phase difference θ23 between the third harmonic component E3 of the output voltage E and the third harmonic component Id3 of the driving current Id. As is clear from the relations in FIG. 4A, FIG. 4B, and FIG. 4C, the phase differences θ21, θ22, and θ23 are calculated from the following relations.

$$\tan\theta 21 = (I1 \times \sin\theta 11 - Icb1)/(I1 \times \cos\theta 11)$$

$$\tan\theta 22 = (I2 \times \sin\theta 12 - Icb2)/(I2 \times \cos\theta 12)$$

$$\tan\theta 23 = (I3 \times \sin\theta 13 - Icb3)/(I3 \times \cos\theta 13)$$

Figure 5:
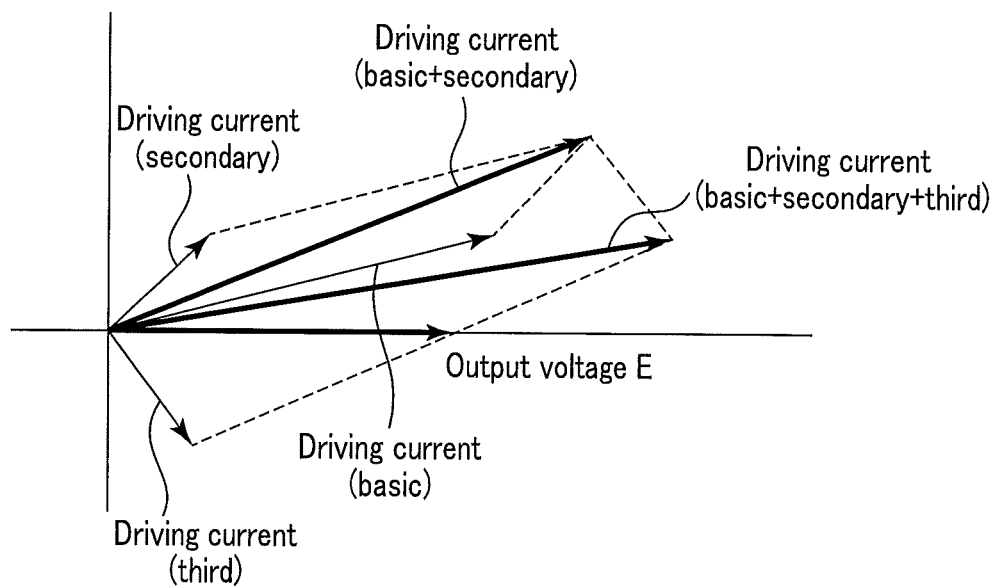
FIG. 5 is a diagram illustrating summing up of the driving current.

The driving current summing unit 1226 calculates the driving current Id, by summing up the absolute value Id1 of the basic component, the absolute value Id2 of the secondary harmonic component, and the absolute value Id3 of the third harmonic component of the driving current Id, based on the absolute value Id1 of the basic component, the absolute value Id2 of the secondary harmonic component, and the absolute value Id3 of the third harmonic component of the driving current Id, and the phase differences θ21, θ22, and θ23. FIG. 5 is a diagram illustrating summing up of the absolute value Id1 of the basic component, the absolute value Id2 of the secondary harmonic component, and the absolute value Id3 of the third harmonic component of the driving current Id. As illustrated in FIG. 5, the ultimate driving current Id is obtained by adding up the basic component Id1, the secondary harmonic component Id2, and the third harmonic component Id3 in a vector manner.

The constant current controller 1227 generates constant current control data based on the driving current Id. For example, the constant current controller 1227 compares the driving current Id calculated by the driving current summing unit 1226 with a target value determined in advance in accordance with the amplitude of the ultrasonic transducer 14, generates constant current control data to remove a difference between the driving current Id and the target value, and outputs the generated constant current control data to the D/A circuit 124.

The frequency controller 1228 outputs frequency control data to the D/A circuit 124. The frequency controller 1228 also performs scan processing to detect the resonant frequency Fr based on the phase difference between the output voltage E and the driving current Id.

Figure 6:
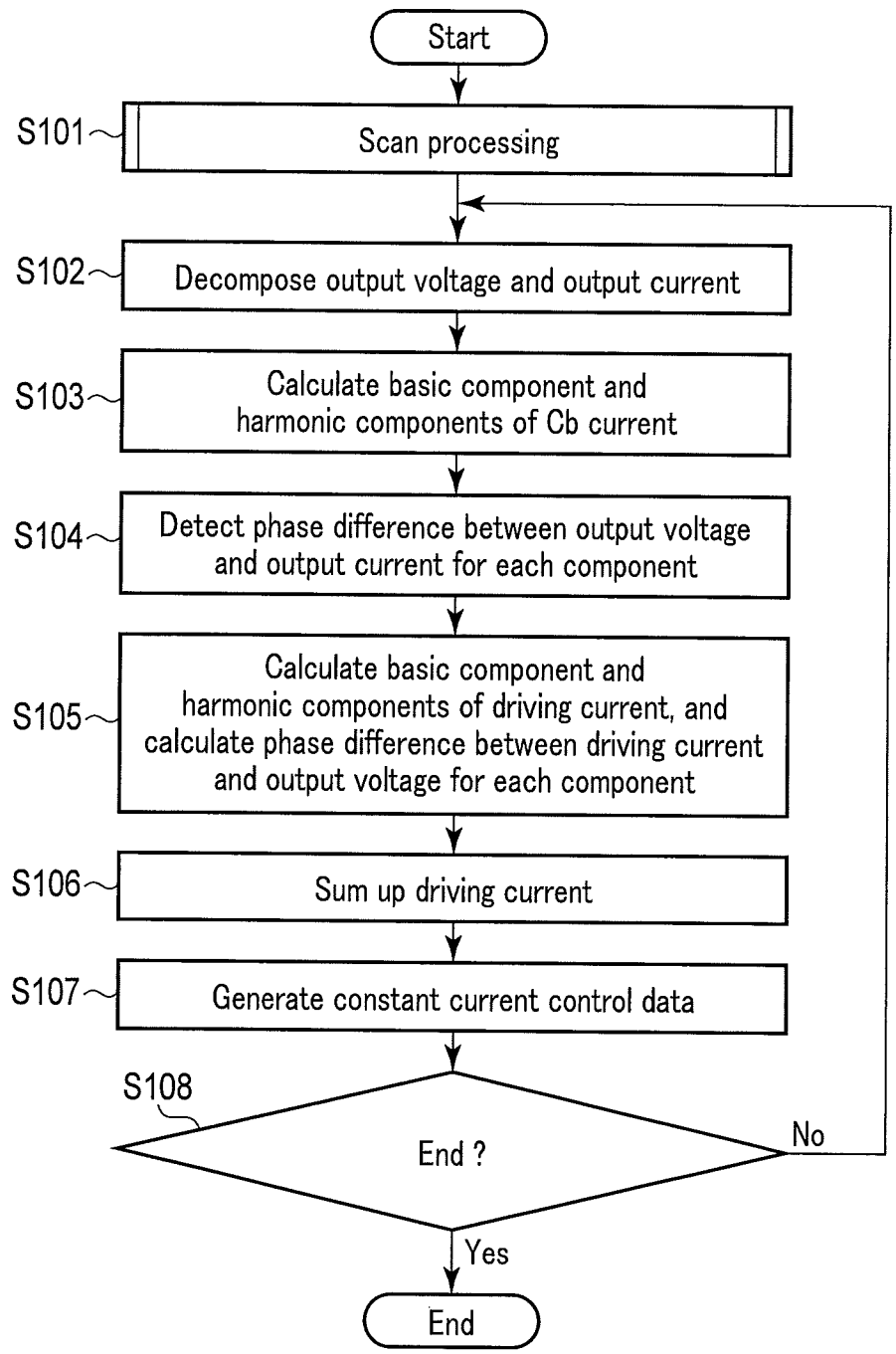
FIG. 6 is a flowchart illustrating operations of the ultrasonic operation apparatus according to one embodiment of the present invention.

The following is explanation of operations of the ultrasonic operation apparatus 1 according to the present embodiment. FIG. 6 is a flowchart illustrating operations of the ultrasonic operation apparatus 1. The process in FIG. 6 is performed, for example, when the operator issues an instruction to start operation of the ultrasonic operation apparatus 1.

Figure 7:
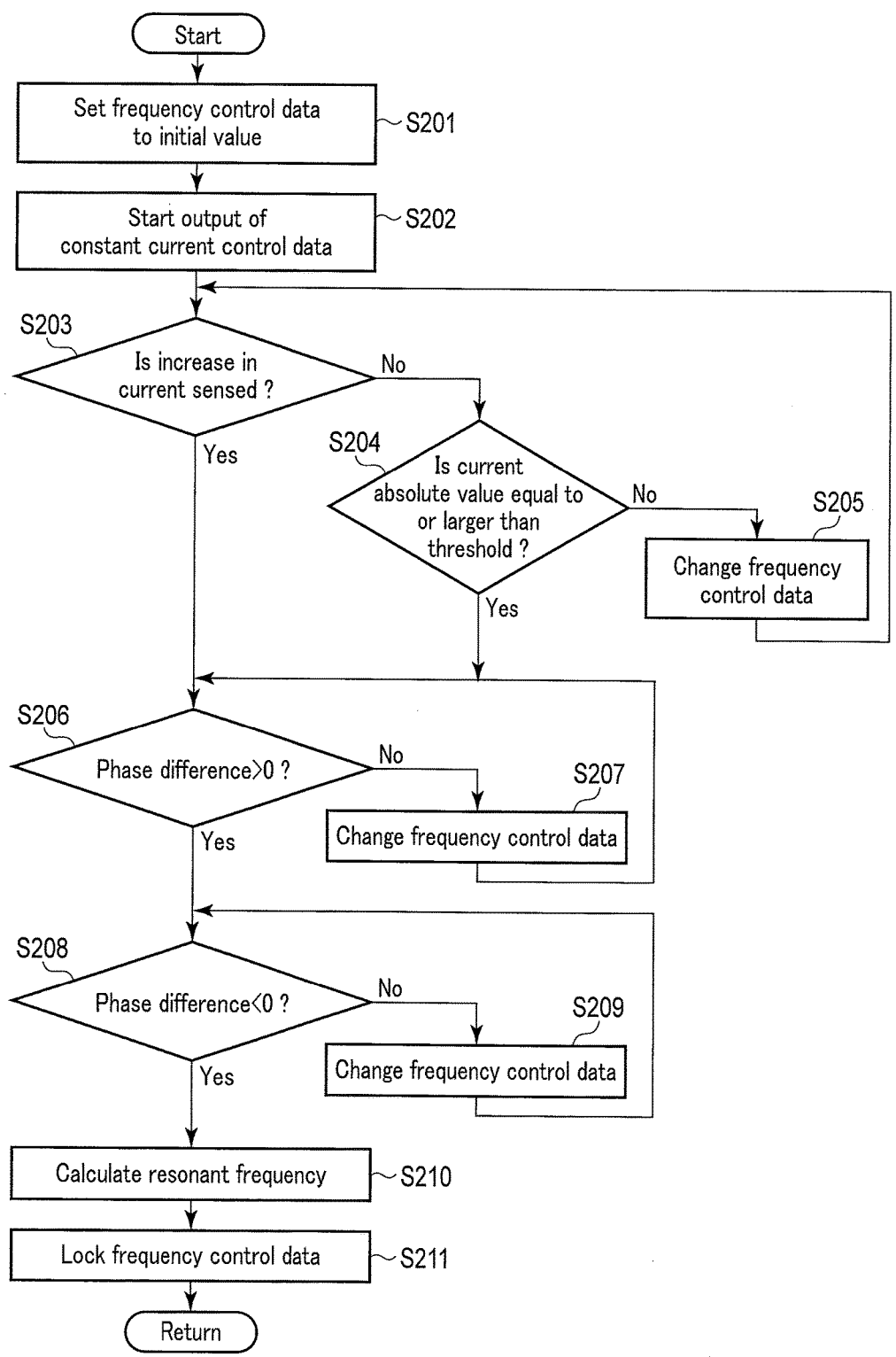
FIG. 7 is a flowchart illustrating scan processing.

In Step S101, the frequency controller 1228 performs scan processing. The scan processing is processing to detect the resonant frequency Fr of the ultrasonic transducer 14. The scan processing will be explained hereinafter with reference to FIG. 7. FIG. 7 is a flowchart illustrating the scan processing.

In Step S201, the frequency controller 1228 sets frequency control data to an initial value. The initial value is set to, for example, a value sufficiently higher than the value of the resonant frequency estimated from the property of the ultrasonic transducer 14 and the like. For example, when the resonant frequency is estimated to be around 47 kHz, the initial value is set to 48 kHz. The setting is a mere example.

In Step S202, the frequency controller 1228 causes the constant current controller 1227 to output constant current control data for scan processing. In this manner, vibration of the ultrasonic transducer 14 is started. The constant current control data for scan processing is predetermined fixed data.

In Step S203, the frequency controller 1228 determines whether an increase in the driving current Id that is equal to or larger than a threshold is sensed. The driving current Id is calculated in the same manner as Step S102 to Step S106 of FIG. 6. In Step S203, when it is determined that no increase in the driving current Id that is equal to or larger than the threshold is sensed, the process goes to Step S204. In Step S203, when it is determined that an increase in the driving current Id that is equal to or larger than the threshold is sensed, the process goes to Step S206. Rapid increase in the driving current Id means that the current frequency is close to the resonant frequency Fr.

In Step S204, the frequency controller 1228 determines whether the absolute value of the driving current Id is equal to or larger than a threshold. In Step S204, when it is determined that the absolute value of the driving current Id is not equal to or larger than the threshold, the process goes to Step S205. In Step S204, when it is determined that the absolute value of the driving current Id is equal to or larger than the threshold value, the process goes to Step S206. The large absolute value of the driving current Id means that the current frequency is close to the resonant frequency Fr.

In Step S205, the frequency controller 1228 changes the frequency control data. Thereafter, the process returns to Step S203. For example, the frequency controller 1228 changes the frequency control data to lower the frequency.

In Step S206, the frequency controller 1228 determines whether the phase difference between the output voltage E and the driving current Id is larger than zero. In Step S206, when it is determined that the phase difference between the output voltage E and the driving current Id is not larger than zero, the process goes to Step S207. In Step S206, when it is determined that the phase difference between the output voltage E and the driving current Id is larger than zero, the process goes to Step S208.

In Step S207, the frequency controller 1228 changes the frequency control data. Thereafter, the process returns to Step S206. For example, the frequency controller 1228 changes the frequency control data to lower the frequency.

In Step S208, the frequency controller 1228 determines whether the phase difference between the output voltage E and the driving current Id is smaller than zero. In Step S206, when it is determined that the phase difference between the output voltage E and the driving current Id is not smaller than zero, the process goes to Step S209. In Step S208, when it is determined that the phase difference between the output voltage E and the driving current Id is smaller than zero, the process goes to Step S210. Sensing both the state in which the phase difference between the output voltage E and the driving current Id is larger than zero and the state in which the phase difference therebetween is smaller than zero means that the state in which the phase difference therebetween is zero, that is, the resonant frequency Fr exists between them.

In Step S209, the frequency controller 1228 changes the frequency control data. Thereafter, the process returns to Step S208. For example, the frequency controller 1228 changes the frequency control data to lower the frequency.

In Step S210, the frequency controller 1228 calculates the resonant frequency Fr. The resonant frequency Fr is a frequency with a phase difference of zero, and calculated by interpolation using the frequency in the state where the phase difference is larger than zero and the frequency in the state where the phase difference is smaller than zero.

In Step S211, the frequency controller 1228 locks the frequency control data to the value corresponding to the resonant frequency Fr. Thereafter, the process of FIG. 7 is ended, and the process goes to Step S102 of FIG. 6.

Figure 8A:
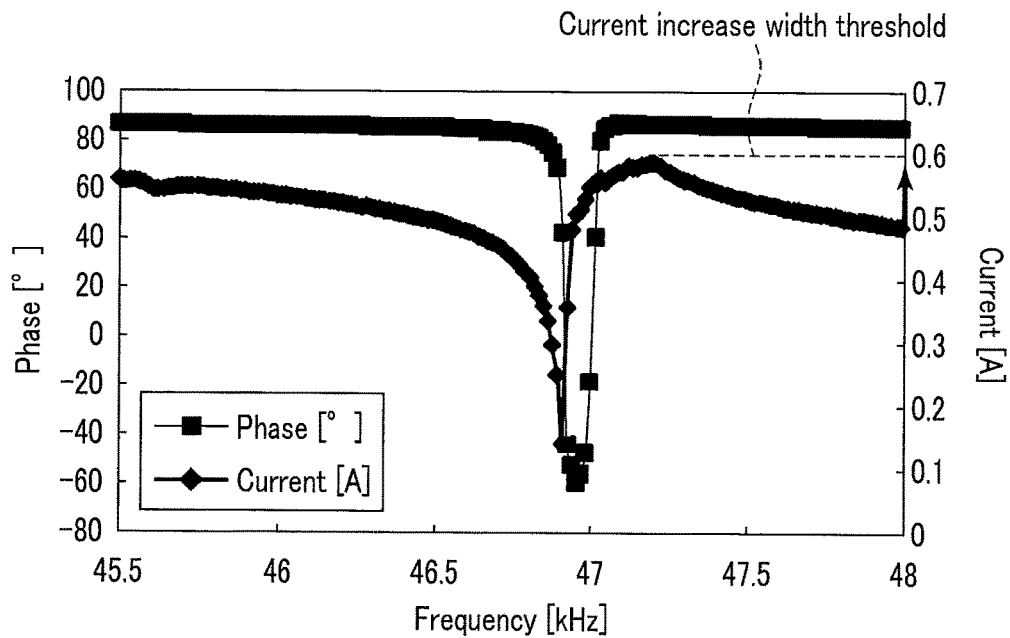
FIG. 8A is a first diagram illustrating an effect of the scan processing according to one embodiment of the present invention.
Figure 8B:
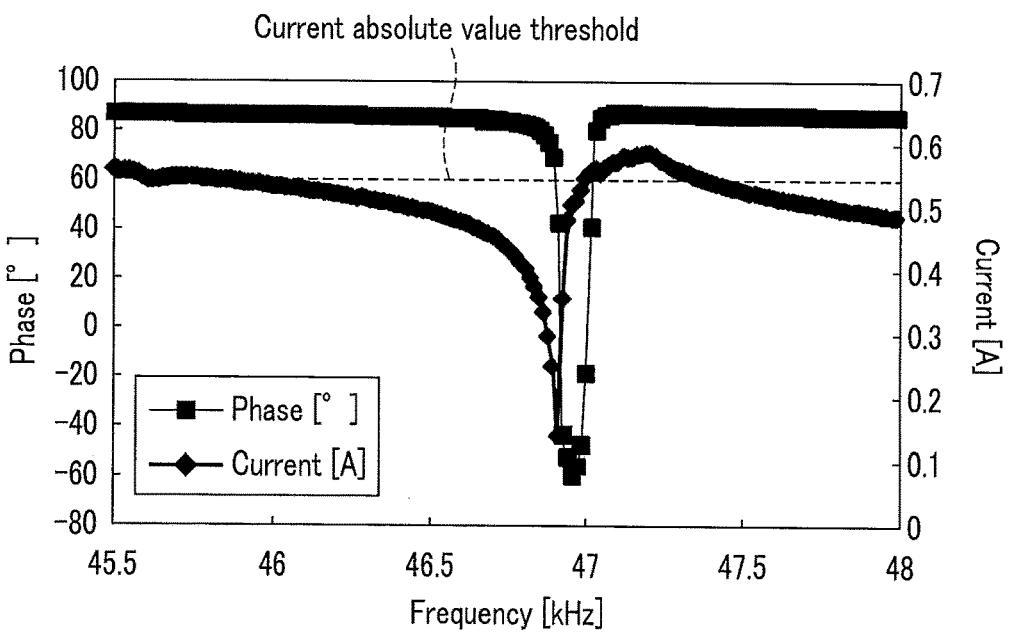
FIG. 8B is a second diagram illustrating the effect of the scan processing according to one embodiment of the present invention.

In the scan processing of FIG. 7, not only the change amount of the driving current Id but also the absolute value of the driving current Id is used for determining whether to go to the processing of sensing the phase difference. In the case where only the change amount of the driving current Id is used for determining whether to go to the processing of sensing the phase difference, the process does not go to the processing of sensing the phase difference, when the driving current Id is large at the point in time of starting the scan processing as illustrated in FIG. 8A and an increase in the driving current Id that is equal to or larger than the threshold cannot be sensed. By contrast, by using also the absolute value of the driving current Id for determining whether to go to the processing of sensing the phase difference, the process is enabled to go to the processing of sensing the phase difference, even when a sufficient change in the driving current Id cannot be sensed as illustrated in FIG. 8B.

The process in FIG. 7 is not necessarily performed when an instruction to start the operation of the ultrasonic operation apparatus 1 is issued. For example, the process in FIG. 7 may be performed only when the power of the ultrasonic operation apparatus 1 is turned on.

The following is explanation of FIG. 6 again. After the ultrasonic transducer 14 starts vibration at the resonant frequency Fr, in Step S102, the output voltage decomposing unit 1221 decomposes the output voltage E into a basic component E1, a secondary harmonic component E2, and a third harmonic component E3. The output current decomposing unit 1222 decomposes the output current I into a basic component I1, a secondary harmonic component I2, and a third harmonic component I3.

In Step S103, the Cb current calculator 1223 obtains an electrostatic capacitance value Cb of the damper capacitor Cb from the Cb storage unit 1223a. The Cb current calculator 1223 calculates a basic component Icb1, a secondary harmonic component Icb2, and a third harmonic component Icb3 of the Cb current Icb, from the basic component E1, the secondary harmonic component E2, and the third harmonic component E3 of the output voltage, the resonant frequency Fr, and the electrostatic capacitance value Cb of the damper capacitor Cb.

In Step S104, the phase difference detector 1224 detects a phase difference $\theta 11$ between the basic component E1 of the output voltage E and the basic component I1 of the output current I, a phase difference $\theta 12$ between the secondary harmonic component E2 of the output voltage E and the secondary harmonic component I2 of the output current I, and a phase difference $\theta 13$ between the third harmonic component E3 of the output voltage E and the third harmonic component I3 of the output current I.

In Step S105, the driving current calculator 1225 calculates the absolute value Id1 of the basic component, the absolute value Id2 of the secondary harmonic component, and the absolute value Id3 of the third harmonic component of the driving current Id, and calculates a phase difference $\theta 21$ between the basic component E1 of the output voltage E and the basic component Id1 of the driving current Id, a phase difference $\theta 22$ between the secondary harmonic component E2 of the output voltage E and the secondary harmonic component Id2 of the driving current Id, and a phase difference $\theta 23$ between the third harmonic component E3 of the output voltage E and the third harmonic component Id3 of the driving current Id.

In Step S106, the driving current summing unit 1226 calculates the driving current Id, by summing up the basic component Id1, the secondary harmonic component Id2, and the third harmonic component Id3, based on the absolute value of the basic component Id1, the absolute value of the secondary harmonic component Id2, and the absolute value of the third harmonic component Id3 of the driving current Id, and the phase differences $\theta 21$, $\theta 22$, and $\theta 23$.

In Step S107, the constant current controller 1227 generates constant current control data based on the driving current Id. In this manner, the value of the driving current Id of the ultrasonic transducer 14 is fixed, and the amplitude of the ultrasonic transducer 14 is also fixed.

In Step S108, the constant current controller 1227 determines whether to end the process of FIG. 6. For example, it is determined that the process of FIG. 6 is ended, when the operator issues an instruction to end the operation of the ultrasonic operation apparatus 1. When it is determined in Step S108 that the process of FIG. 6 is not ended, the process returns to Step S102. When it is determined in Step S108 that the process of FIG. 6 is ended, the process is ended.

As described above, the present embodiment enables constant current control to fix the driving current contributing to vibration of the ultrasonic transducer 14. The output current flowing through the ultrasonic transducer 14 includes the driving current and the Cb current. Both the driving current and the Cb current include harmonic components. In the present embodiment, first, the basic component and the harmonic components of the Cb current are determined, the basic component and the harmonic components of the driving current are determined thereafter, and the components are summed up. This structure enables separation of only the driving current from the output current. Constant current control to fix the driving current separated as described above enables highly accurate control of the vibration amplitude of the ultrasonic transducer 14.

Modification 1

The following is explanation of a modification of the present embodiment. In the embodiment described above, the output voltage decomposing unit 1221 decomposes the output voltage E into a basic component E1, a secondary harmonic component E2, and a third harmonic component E3. In addition, the output current decomposing unit 1222 decomposes the output current I into a basic component I1, a secondary harmonic component I2, and a third harmonic component I3. However, the number of decomposed components is not limited thereto. Specifically, the output voltage decomposing unit 1221 and the output current decomposing unit 1222 may be configured to decompose the output voltage E and the output current I, respectively, into a basic component and a secondary harmonic component, or into a basic component and harmonic components up to fourth or more harmonic components.

Modification 2

Figure 9:
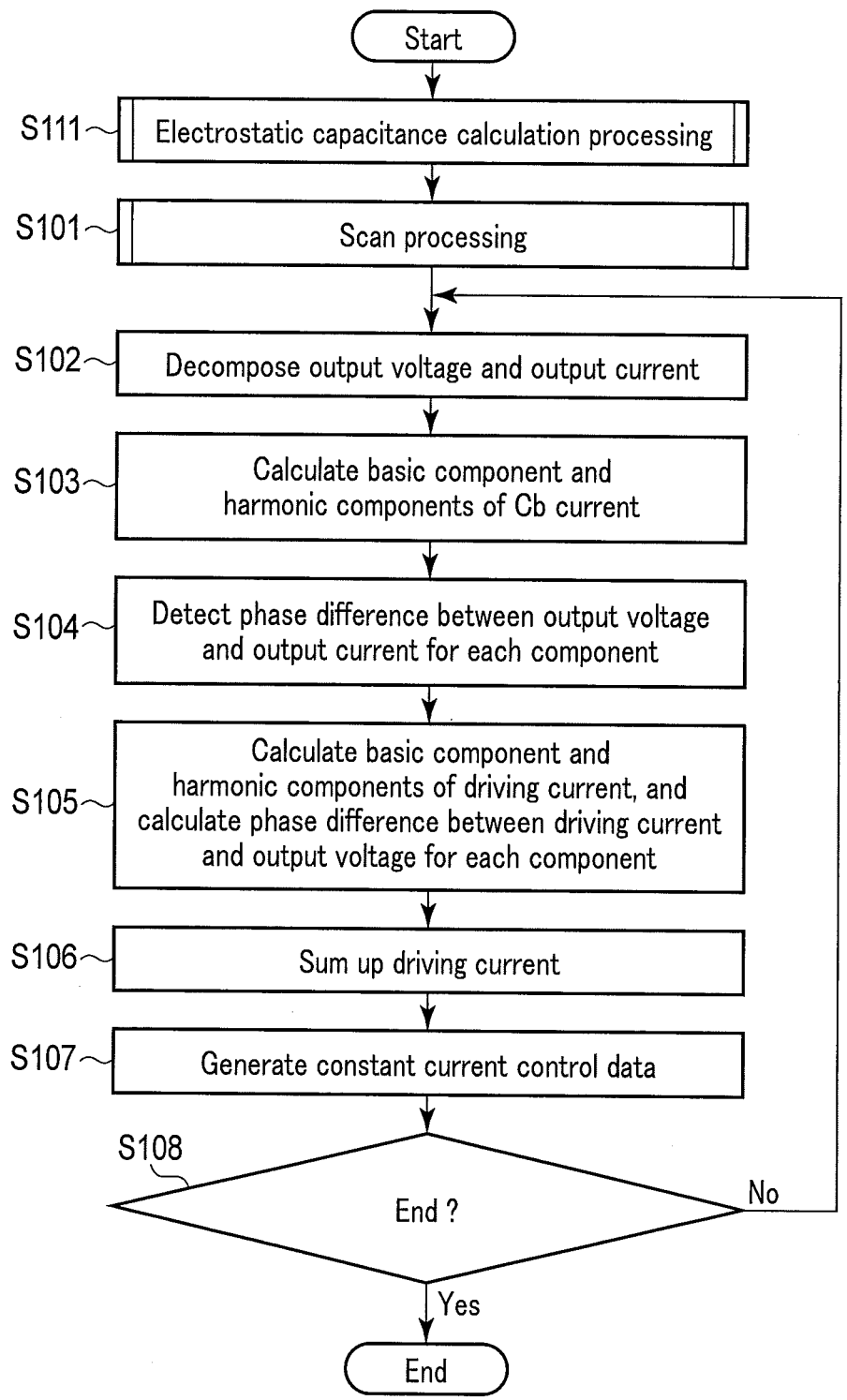
FIG. 9 is a flowchart illustrating operations of an ultrasonic operation apparatus according to Modification 2.
Figure 10:
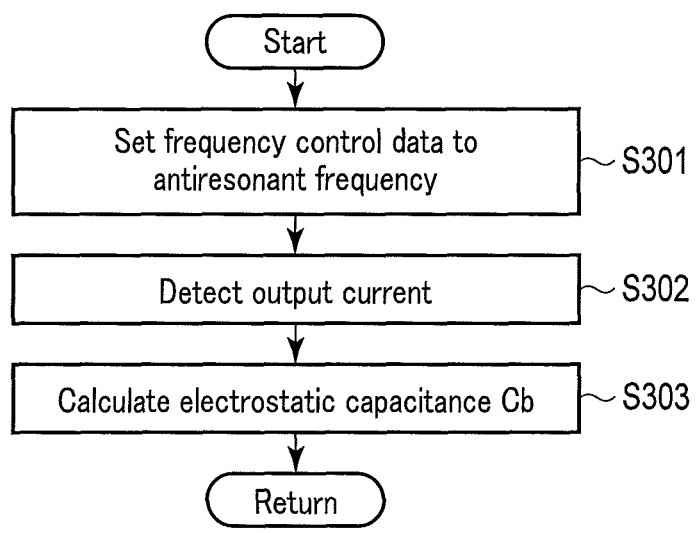
FIG. 10 is a flowchart illustrating electrostatic capacitance calculation processing.

In the embodiment described above, the electrostatic capacitance value Cb of the damper capacitor Cb is a fixed value. By contrast, the electrostatic capacitance value Cb may be measured at the time when the ultrasonic operation apparatus 1 starts operation or the power of the ultrasonic operation apparatus 1 is turned on. The following is explanation of the modification. FIG. 9 is a flowchart illustrating operations of the ultrasonic operation apparatus 1 according to Modification 2. The process of FIG. 9 is the same as the process of FIG. 6 except that electrostatic capacitance calculation processing is performed in the first Step S111. Accordingly, the electrostatic capacitance calculation processing is explained hereinafter. FIG. 10 is a flowchart illustrating the electrostatic capacitance calculation processing.

In Step S301, the frequency controller 1228 sets the frequency control data to a value corresponding to an antiresonant frequency Far. The antiresonant frequency Far is a frequency at which the phase difference between the output voltage E and the output current I becomes maximum (90°). The antiresonant frequency Far is obtained by, for example, successively changing the frequency control data in the same manner as FIG. 7, and locking the frequency when the phase difference between the output voltage E and the output current I becomes maximum.

In Step S302, the Cb current calculator 1223 detects the output current I. When the equivalent circuit of FIG. 3 is driven with the antiresonant frequency, the series resonant circuit SRC can be regarded as being opened. In this state, the output current I agrees with the Cb current Icb. Specifically, when the equivalent circuit of FIG. 3 is driven with the antiresonant frequency, the Cb current Icb can be detected by detecting the output current I.

In Step S303, the Cb current calculator 1223 calculates the electrostatic capacitance value Cb of the damper capacitor Cb. Thereafter, the process of FIG. 10 is ended, and the process goes to Step S101 of FIG. 9. The electrostatic capacitance value Cb is calculated as follows, for example.

$$Cb = Icb/(2\pi \times Far \times E) = I/(2\pi \times Far \times E)$$

Modification 2 explained above enables more accurate calculation of the Cb current, with the electrostatic capacitance value Cb that is not a fixed value.

The processes performed by the embodiment described above may be stored as a program that can be executed by a CPU or the like serving as a computer. Otherwise, the processes may be stored and distributed in a storage medium of an external storage device such as a memory card, a magnetic disk, an optical disk, and a semiconductor memory. The CPU or the like can execute the processes described above, by reading the program stored in the storage medium of the external storage device, and being controlled by the read program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A driving device electrically connected with an ultrasonic treatment tool, wherein the ultrasonic treatment tool including an ultrasonic transducer for treating a living tissue by ultrasonic vibration generated by the ultrasonic transducer, the ultrasonic transducer being represented by an electrical equivalent circuit in which a second capacitor is connected in parallel with a series circuit formed of an inductor, a first capacitor, and a resistor, the driving device comprising:
   a control circuit configured to:
      decompose an output voltage applied to the ultrasonic transducer by an alternating-current driving voltage to drive the ultrasonic transducer into a basic component and a harmonic component;
      decompose an output current flowing through the ultrasonic transducer by the driving voltage into a basic component and a harmonic component;
      calculate a basic component and a harmonic component of a capacitor current flowing through the second capacitor, based on the basic component and the harmonic component of the output voltage and an electrostatic capacitance value of the second capacitor;
      calculate a basic component and a harmonic component of a driving current flowing through the series circuit, based on the basic component and the harmonic component of the output current and the basic component and the harmonic component of the capacitor current flowing through the second capacitor;
      sum up the basic component and the harmonic component of the driving current; and
      generate constant current control data to control the driving voltage such that the driving current has a target value.

2. The driving device according to claim 1, further comprising:
   a memory storing the electrostatic capacitance value of the second capacitor,
   wherein the control circuit obtains the electrostatic capacitance value of the second capacitor from the memory.

3. The driving device according to claim 1, wherein the control circuit calculates the electrostatic capacitance value of the second capacitor, based on the output current flowing through the ultrasonic transducer when the ultrasonic transducer is driven with an antiresonant frequency.

4. The driving device according to claim 1, wherein the control circuit calculates the basic component of the driving current by subtracting the basic component of the capacitor current flowing through the second capacitor from the basic component of the output current, based on a phase difference between the basic component of the output voltage and the basic component of the output current, and calculates the harmonic component of the driving current by subtracting the harmonic component of the capacitor current flowing through the second capacitor from the harmonic component of the output current, based on a phase difference between the harmonic component of the output voltage and the harmonic component of the output current.

5. The driving device according to claim 1, wherein the control circuit sums up the basic component and the harmonic component of the driving current, based on a phase difference between the basic component of the output voltage and the basic component of the driving current and a phase difference between the harmonic component of the output voltage and the harmonic component of the driving current.

6. A method for controlling a driving device electrically connected with an ultrasonic treatment tool, wherein the ultrasonic treatment tool including an ultrasonic transducer for treating a living tissue by ultrasonic vibration generated by the ultrasonic transducer, the ultrasonic transducer being represented by an electrical equivalent circuit in which a second capacitor is connected in parallel with a series circuit formed of an inductor, a first capacitor, and a resistor, the method comprising:
   decomposing an output voltage applied to the ultrasonic transducer by an alternating-current driving voltage to drive the ultrasonic transducer into a basic component and a harmonic component;
   decomposing an output current flowing through the ultrasonic transducer by the driving voltage into a basic component and a harmonic component;
   calculating a basic component and a harmonic component of a capacitor current flowing through the second capacitor, based on the basic component and the harmonic component of the output voltage and an electrostatic capacitance value of the second capacitor;
   calculating a basic component and a harmonic component of a driving current flowing through the series circuit, based on the basic component and the harmonic component of the output current and the basic component and the harmonic component of the capacitor current flowing through the second capacitor;
   summing up the basic component and the harmonic component of the driving current; and
   generating constant current control data to control the driving voltage such that the summed driving current has a target value.

* * * * *